United States Patent [19]

Fang

[11] 3,954,715
[45] May 4, 1976

[54] COATING COMPOSITIONS CONTAINING DIESTERS OF DIBASIC ACIDS AND GLYCIDYL ESTERS AND AMINOPLAST RESINS

[75] Inventor: James C. Fang, Media, Pa.

[73] Assignee: E. I. Du Pont de Nemours and Company, Wilmington, Del.

[22] Filed: Aug. 1, 1974

[21] Appl. No.: 493,971

Related U.S. Application Data

[62] Division of Ser. No. 338,055, March 5, 1973, abandoned.

[52] U.S. Cl. .................. 260/67.6 R; 260/31.8 T; 260/33.2 R; 260/67.6 C; 260/69 R; 260/72 R; 260/851; 260/856
[51] Int. Cl.² .................. C08K 5/11; C08L 61/24; C08L 61/26; C08L 61/28
[58] Field of Search .......... 260/67.6 R, 851, 31.8 T, 260/33.2 R, 68, 69 R, 72.5, 67.6 C, 850, 856, 72 R

[56] References Cited

UNITED STATES PATENTS

| | | | |
|---|---|---|---|
| 3,234,249 | 2/1966 | Brack | 260/67.6 R |
| 3,442,873 | 5/1969 | Vasta | 260/851 |
| 3,642,739 | 2/1972 | Van Gogh et al. | 260/851 |
| 3,673,148 | 6/1972 | Vasta | 260/851 |

*Primary Examiner*—Allan Lieberman

[57] ABSTRACT

Esters of dibasic unsaturated acids and glycidyl esters, when formulated with aminoplast resins, form coating compositions which require little or no organic liquid carrier. These compositions are useful as primers in the finishing of appliances and automobiles, and for general industrial use.

4 Claims, No Drawings

COATING COMPOSITIONS CONTAINING DIESTERS OF DIBASIC ACIDS AND GLYCIDYL ESTERS AND AMINOPLAST RESINS

CROSS-REFERENCE TO RELATED APPLICATION

This application is a divisional of application Ser. No. 338,055, filed Mar. 5, 1973, now abandoned.

BACKGROUND OF THE INVENTION

There has been much emphasis in recent years on developing coating compositions which do not pollute the atmosphere as they dry. This has become increasingly important with the passage of legislation strictly limiting the amounts and kinds of organic liquids that can be emitted during industrial finishing operations.

The diesters of my invention, when formulated with aminoplast resins, form coating compositions which require little or no organic liquid carrier to bring them to application viscosity. These compositions therefore emit a minimum of volatiles into the air as they cure.

Their low liquid content also carries with it additional benefits. Since my compositions have an extremely high film-forming solids content, the saving in shipping costs is considerable. Their high solids content also makes it possible, in spray applications, to apply more of the composition per pass of the spray gun, thereby saving much in labor costs.

My compositions also have the advantage of being compatible with most conventional mill bases used in the paint industry to pigment coating compositions.

In addition, when cured by conventional baking techniques, my compositions give hard, durable, flexible finishes with excellent hydrolytic stability, good resistance to attack by alkali and detergents and excellent adhesion to unprimed metal.

All these properties suit my compositions for use as primers in finishing appliances, metal furniture and automobiles.

SUMMARY OF THE INVENTION

The diesters of my invention are those of unsaturated dibasic acids with glycidyl esters. More particularly my esters are those represented by the structural formula

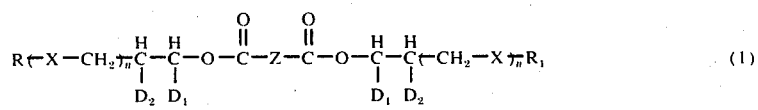  (1)

where Z is

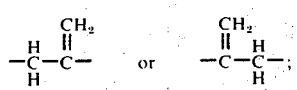

$D_1$ is hydrogen, —OH or —$CH_2OH$;
$D_2$ is hydrogen or —$OH_2$ (but one of $D_1$ or $D_2$ must be —$CH_2OH$ or —OH);
X is

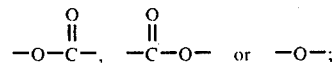

R and $R_1$ are alkyl radicals of 4-18 carbon atoms; and $n$ is 0 or 1.

The diester I prefer is that represented by formula (1), where Z is

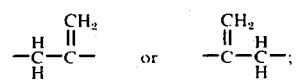

$D_1$ is hydrogen;
$D_2$ is —OH;
X is

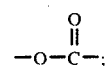

$n$ is 1;
and
R and $R_1$ are

where $R_2$ is —$CH_3$ and $R_3$ and $R_4$ are lower alkyl, the total of carbon atoms in $R_2$, $R_3$, and $R_4$ being 7–11.

Preparation of the Diesters

I first react about 1 mol of a suitable dibasic unsaturated acid with about 2 mols of a suitable glycidyl ester, glycidyl ether or alkylene oxide, according to the illustrative equation -continued

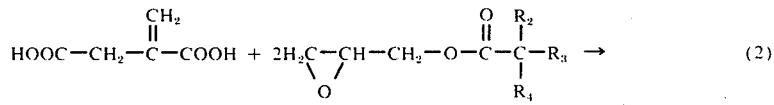

(2)

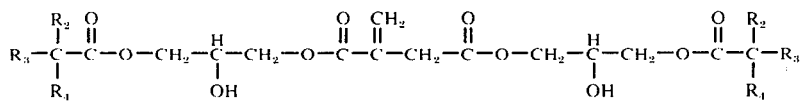

I catalyze this reaction with about 1% by weight, of zinc dioctoate, zinc octoate-triphenyl phosphite complex, tin dioctoate, toluenesulfonic acid or tetrapropyl titanate.

I mix the acid and glycidyl compound and then hold this mixture at 140°–200°C., preferably 140°–160°C., for about 30 minutes. Preparation of my diester is then complete.

The dibasic unsaturated acids I use in this process are fumaric, maleic and itaconic. Maleic anhydride can also be used. I prefer to use itaconic acid.

Illustrative of the glycidyl compounds which can be used are esters of glycidol with monobasic acids of 4-18 carbon atoms, such as glycidyl palmitate, glycidyl laurate and glycidyl stearate; alkylene oxides of 4–18 carbon atoms such as butylene oxide; and glycidyl ethers such as octyl glycidyl ether. I especially prefer to use a mixed glycidyl ester known as "Cardura E" ester[1] which is represented by the structure

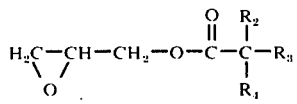

where $R_2$ is —$CH_3$ and $R_3$ and $R_4$ are lower alkyl, the total number of carbon atoms in $R_2$, $R_3$ and $R_4$ being 7–11.

[1]Sold by Shell Chemical Company

It will be apparent from the foregoing equations that small amounts of isomers of the product shown will be formed. For example, when maleic acid is used, the product will partially isomerize to the trans form (fumaric acid).

Also, the hydroxyl group or —$CH_2OH$ group [$D_1$ or $D_2$ in formula (1)[ which results from rupturing the cyclic ether ring of glycidyl compound may be attached in either of the positions shown. These isomeric forms can be isolated from the main product by chromatographic techniques, if this is desired. But I have found that isolation is unnecessary because all of the isomers are useful for the purposes I have already described. Indeed, the presence of these isomeric forms in some cases makes the compositions compatible with a wider variety of film-formers and lowers their viscosity. I therefore prefer and recommend that the various isomers not be isolated.

In preparing my diesters one may use mixtures of acids and of glycidyl compounds if he wishes to obtain a balance of properties.

How My Diesters Are Used

I mix the product of the foregoing preparation scheme with a conventional aminoplast resin such as a melamine-formaldehyde resin, a benzoguanamine-formaldehyde resin, a urea-formaldehyde resin, a melamine toluenesulfonamide resin, a hexamethoxymethylmelamine resin, or any of the alkylated melamine-formaldehyde, benzoguanamine-formaldehyde or urea-formaldehyde resins. I prefer to use a hexamethoxymethylmelamine resin.

I prepare this mixture so that it contains approximately 50–80%, by weight of the total, of my diester and approximately 20% to about 50%, by weight of the total of the aminoplast resin.

After the components have been thoroughly mixed, I add a pigment, if this is desired, by way of a conventional mill base. This mill-base can be based, for example, on an alkyd resin or a low molecular weight acrylic resin. The amount of mill base used is conventional and will depend on the depth of color desired. Generally speaking, no compatibility problems will be encountered, for my coating compositions are compatible with most mill bases conventionally used in the industry. Preparation of the coating composition is then complete.

All that is required to reduce my coating compositions to application viscosity is to heat them to approximately 40°–55°C. The compositions can also be reduced to application viscosity by the addition of such conventional thinners as toluene, methylethyl ketone or acetone. In general, this causes no problems for my compositions are also compatible with most such organic liquids. However, I find this dilution to be unnecessary, for it only introduces organic liquids into my compositions which the law now requires to be at low concentration or completely absent, and whose presence confers no special advantages.

However my compositions are thinned, they are ordinarily sprayed to whatever substrate is being coated, although other techniques such as brushing, dipping, roller-coating or doctor-blading can be employed. If spray application is the method of choice, those skilled in the art will be pleased to note that no special spraying equipment or techniques are required. My compositions can be conventionally sprayed with no loss of quality or economy.

The thickness to which my compositions are applied is largely a matter of choice, but as already mentioned, it is possible in most cases to apply somewhat thicker coats than is the rule with conventional coating compositions without the accompanying sagging and running.

My compositions, however they are applied, are then cured by baking them for approximately one-half hour at 120°–180°C. to give hard, durable, flexible, strongly adherent finishes.

If my compositions are used as primers, these finishes can be topcoated with any composition suitable for this purpose, using customary techniques.

DESCRIPTION OF THE PREFERRED EMBODIMENTS

Those skilled in the polymer and paint art will be able to practice my invention with greater ease after having read the following illustrative examples. I recognize that these artisans will be able to compose numerous variations on the examples' theme, such as the introduction of substituents, not shown here, onto the basic molecule, and the use of conventional adjuncts. I consider all of these variations to be within my inventive concept.

EXAMPLE 1

The following were mixed together in a reaction kettle:

|  | Parts |
| --- | --- |
| Itaconic acid | 130 |
| "Cardura E" | 400 |
| Methoxyphenol | 0.1 |
| Zinc octoate-triphenylphosphite complex* | 2.00 |

*An epoxy resin catalyst known as DB VIII, sold by Argus Chemical Corp.

The mixture was heated to 140°–160°C., with stirring, and held there for about 30 minutes to give a pale yellow liquid like heavy mineral oil in viscosity.

Maleic acid and fumaric acid can be substituted for itaconic acid in this process, in equivalent molar amounts, with substantially the same result. Similarly, butylene oxide can be substituted for "Cardura E".

Example 2

The following were thoroughly mixed:

|  | Parts |
| --- | --- |
| Product of Example 1 | 240 |
| Hexamethoxymethylmelamine | 75 |
| Mill base | 540 |
| Composed of |  |
| TiO$_2$ | 63% |
| Non-drying oil alkyd resin (60% solids in toluene/xylene 50/50) | 23.5% |
| Toluene | 13.5% |

This mixture was heated to 40°–50°C. and then sprayed to a Bonderized unprimed steel panel to a thickness of 1.5 mils (dry). The panel was baked for one-half hour at 165°C. to give a hard, glossy, durable, flexible adherent coating.

The products of Example 1, wherein maleic and fumaric acids are substituted for itaconic acid, and where butylene oxide is substituted for Cardura E, can be used in place of the product of Example 1, in the same amount, with substantially the same result.

I claim:

1. A coating composition consisting essentially of
   a. approximately 50–80%, by weight of the total, of a compound represented by the structure

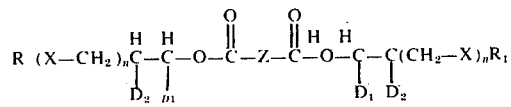

where
Z is

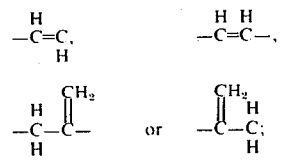

$D_1$ is hydrogen, —OH or —CH$_2$OH; $D_2$ is hydrogen or —OH, (but one of $D_1$ or $D_2$ must be —OH or —CH$_2$OH);
X is

or —O—;
R and R$_1$ are alkyl radicals of 4–18 carbon atoms; and
$n$ is 0 or 1; and
   b. approximately 20–50%, by weight of the total, of an aminoplast resin.

2. The composition of claim 1 where, in the compound of (a),
Z is

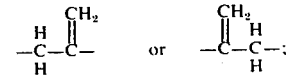

$D_1$ is hydrogen;
$D_2$ is —OH;
X is

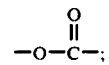

$n$ is 1; and
R and R$_1$ are

where R$_2$ is —CH$_3$ and R$_3$ and R$_4$ are lower alkyl, the total numbers of carbon atoms in R$_2$, R$_3$, and R$_4$ being 7–11.

3. The coating composition of claim 1 wherein the aminoplast resin is a hexamethoxymethyl melamine resin.

4. The coating composition of claim 2 wherein the aminoplast resin is a hexamethoxymethyl melamine resin.

* * * * *